United States Patent [19]

Mosbach et al.

[11] Patent Number: 4,647,536

[45] Date of Patent: Mar. 3, 1987

[54] METHOD OF ENCAPSULATING BIOMATERIAL IN BEAD POLYMERS

[76] Inventors: Klaus Mosbach, Lackalänga 31, S-244 02 Furulund; Kjell Nilsson, Fågelhundsv. 30, 222 53 Lund, both of Sweden

[21] Appl. No.: 552,044

[22] PCT Filed: Mar. 8, 1983

[86] PCT No.: PCT/SE83/00074

§ 371 Date: Nov. 8, 1983

§ 102(e) Date: Nov. 8, 1983

[87] PCT Pub. No.: WO83/03102

PCT Pub. Date: Sep. 15, 1983

[30] Foreign Application Priority Data

Mar. 8, 1982 [SE] Sweden ................................ 8201401

[51] Int. Cl.$^4$ .................... C12N 11/02; A01N 25/00; A01N 63/00
[52] U.S. Cl. ...................................... 435/177; 435/178; 435/182; 424/93; 424/DIG. 7; 424/493
[58] Field of Search ................. 264/4.1, 4.3; 424/32, 424/34–38, 93, 94; 435/177, 182, 178; 514/2

[56] References Cited

U.S. PATENT DOCUMENTS

| | | | |
|---|---|---|---|
| 4,169,804 | 10/1979 | Yapel et al. | 424/36 X |
| 4,352,883 | 10/1982 | Lim | 424/94 X |
| 4,353,888 | 10/1982 | Sefton | 424/32 X |
| 4,389,330 | 6/1983 | Tice et al. | 424/32 X |
| 4,518,693 | 5/1985 | Kuu | 435/178 |

FOREIGN PATENT DOCUMENTS 1404933 9/1975 United Kingdom .
1469072 3/1977 United Kingdom .
1560850 2/1980 United Kingdom .

OTHER PUBLICATIONS

Derwent Abs. 64776 B/36 (1979).

*Primary Examiner*—David M. Naff
*Assistant Examiner*—Shawn P. Foley
*Attorney, Agent, or Firm*—Oblon, Fisher, Spivak, McClelland & Maier

[57] ABSTRACT

Viable biomaterial such as animal cells, plant cells, bacteria, algae or fungi are immobilized with retained ability of growth by encapsulation in polymer beads. Encapsulation is carried out by adding the biomaterial to an aqueous solution of a polymer such as agar, agarose, carrageenan, chitosan, gelatin, collagen or fibrinogen, dispersing the solution in a water-insoluble dispersion medium such as soybean oil, tri-n-butylphosphate, liquid silicone, paraffin oil or phthalic acid dibutylester and allowing the polymer to gel.

6 Claims, No Drawings

METHOD OF ENCAPSULATING BIOMATERIAL IN BEAD POLYMERS

The present invention relates to a method of immobilizing bio material such as animal cells, plant cells, bacteria, algae, fungi, viruses or proteins by encapsulation in bead polymers.

During recent years there has been a considerable interest in immobilizing bio material. The most usual polymers used for encapsulating bio material are alginate, polyacrylamide, carrageenan, agar or agarose. Of these alginate and carrageenan are the only ones which can be manufactured simply in spherical form with encapsulated material. This is done by ionotropic gelling, i.e. the alginate is dropped down into calcium solution and the carrageenan in a potassium solution. However, relatively large beads (2-3 mm diameter) are usually obtained in this way, and beads that are stable only in the presence of ions (calcium and potassium ions, respectively). In the use of agar, agarose, collagen, polyacrylamide, gelatine or fibrinogen, the biomaterial is usually mixed with polymer or polymer solution which is then caused to gel. In order to obtain a suitable size, this gel is fragmented and possibly further cross-linked to attain higher stability. In the preparations produced in this way there is leakage of the encapsulated material in the fragmentation, and due to their heterogeneity they are found to have poor flow in column processes.

Spherical polyacrylamide particles with encapsulated enzymes can be produced by a bead polymerization process, where the monomer solution together with enzyme and catalysts are dispersed in a hydrophobic phase (see Swedish Pat. No. 7204481-1). The hydrophobic phase comprises an organic solvent (exemplified by toluene plus chloroform) and an emulsifier. Since both these solvents and emulsifiers have a denaturing effect, this method is suitable only for relatively insensitive material.

There has therefore been a large need for a more gentle dispersion medium for the production of spherical polymer particles. The present invention discloses that sensitive bio material can be encapsulated with full viability and with retained growth ability if the organic solvent is exchanged for either of the following dispersion media: saturated or unsaturated animal or vegetable fats or oils, tri-n-butylphosphate, liquid silicone, paraffin oil or phthalic acid dibutyl ester. Certain of these dispersion media have been used before in the preparation of spherical polymer particles. In the U.S. Pat. No. 4 169 804 there is described a method of producing magnetic microspheres by dispering an albumin solution in vegetable oil with subsequent heating thereof to 140° C. or cross-linking the albumin polymer with aldehydes. This technique cannot be used for encapsulating sensitive bio material, since either the high temperature or the cross-linking aldehyde then result in inactivation.

A method is described in "Biotechnology Letters" vol. 3, pages 65-70, 1981, of producing spherical polyurethane particles by dispersing the monomers in paraffin oil. By including bacteria in the monomer mixture there is obtained a catalytically active preparation (although whether the bacteria retain their propagating ability is doubtful, furthermore there is great risk that they are linked covalently to the carrier). On the other hand, by combining these gentle dispersion media with a suitable immobilization-method carrier there may be obtained, as with the preparations described here, 100% viability and retained growth ability. The denaturing action of different dispersion media on agar-encapsulated plant cells is compared in table 1. It will be seen from the table that these dispersion media give a retained viability compared with the usual standard method for the production of spherical polymer particles (Swedish patent 7204481-1). In table 2, this relationship is also shown to apply to yeast cells encapsulated in polyacrylamide.

The polymer which is combined with the dispersion medium is selected on the basis of the bio material sensitivity. Insensitive materials such as certain proteins can be linked covalently to the polymer with formaldehyde, after they have been encapsulated, this applying particularly to the polymers gelatine and chitosan. Relatively insensitive bio material such as yeast cells can be encapsulated in polyacrylamide with retained viability. More sensitive systems such as plant cells, algae or animal cells are suitably encapsulated in polymers such as agar, agarose, carrageenan, gelatine, collagen or fibrin.

There are two principally different types of animal cells, suspension cells and surface-dependent cells. The surface-dependent cells must be attached to a surface in order to survive and grow. In this invention the fibres formed by collagen or fibrin are used as the necessary surface, this resulting in the surface-dependent animal cells being able to survive and grow in an encapsulated condition. Surface-dependent cells cannot grow encapsulated in agarose, but by mixing agarose with fibrin or collagen this polymer can also be used for encapsulating surface-dependent cells. Animal suspension cells do not have this requirement and may be encapsulated in agarose, collagen or fibrin with retained ability to grow. Since the potential field of use of animal cells is very large (the production of vaccines, proteins or hormones, transforming of precursors etc) it is important to develop systems where they can be used on a large scale.

Encapsulated animal cells have great advantages, from the aspect of production technique, compared with free cells. For example, they can easily be used in column processes, and there are also advantages in other types of reaction, since they are much easier to adapt to continuous production.

The size of the bead formed with encapsulated bio material can be varied within wide limits, depending on the force with which the polymer solution is dispersed.

EXAMPLE 1

Agar, agarose

Agar or agarose is dissolved in water (5.6% w/v) by heating. The polymer slution (8 ml) is brought to a temperature of 50° C. and mixed with plant cells (2 g) subsequent to which dispersion in soybean oil (40 ml) takes place. When suitably large beads have been obtained the mixture is cooled to 5° C. and the beads washed over to water.

EXAMPLE 2

Carrageenan

The carrageenan is dissolved in 0.9% NaCl (3.1% w/v) by heating. The beads are manufactured according to example 1.

EXAMPLE 3

Chitosan

Chitosan is dissolved in 0.1M HAc/0.1M NaAc. The polymer solution (8 ml) is mixed with yeast cells (2 ml) or enzymes (peroxidase 10 mg/ml, 2 ml) after which it is dispersed in soybean oil (40 ml), and formaldehyde (37% w/v, 2.2 ml) is now added, after which stirring is carried out for 30 minutes. The cross-linked beads are washed over to water.

EXAMPLE 4

Polyacrylamide

Acrylamide (17.6 g) and bisacrylamide (1.2 g) are dissolved in tris-buffer (100 ml, 0.05M, pH7). The monomer solution (8 ml) is mixed with yeast cells or enzymes (peroxidase, 10 mg/ml, 2 ml) and ammonium persulphate (0,4 g/ml, 20 μl) and dispersed in soybean oil (40 ml). TEMED (100 μl) is added when a suitable bead size has been reached. The polymerized beads are washed over to water.

EXAMPLE 5

Gelatine

Gelatine (15% w/v) is dissolved by heating in water. The polymer solution (8 ml) is brought to a temperature 37° C. and mixed with yeast cells (2 ml), subsequent to which it is dispersed in soybean oil (40 ml). After cooling to 15° C., the beads are washed over to water.

EXAMPLE 6

Gelatine capsules

Gelatine (15% w/v) is dissolved in a phosphate buffer (0.1M pH 8). The polymer solution (8 ml) is brought to a temperature 37° C. and mixed with cells (plant cells 2 g), subsequent to which it is dispersed in soybean oil (40 ml) containing a water-soluble cross-linking agent (toluene diisocyanate, 2.5% w/v), the beads being washed over to water after 30 minutes. In heating to 37° C., gelatine which has not been cross-linked goes into solution and leaves the shell intact. Plant cells immobilized in this way are unaffected by the cross-linking agent and are viable to 95% with respect to respiration.

EXAMPLE 7

Fibrinogen

The fibrinogen solution (1 ml, 2% w/v) is mixed with the fibrinogen buffer (1 ml) and fetal calf serum (0.3 ml). Animal cells (0.7 ml) and thrombin (1.5 U) are then added. The mixture is dispersed in paraffin oil (40 ml), and after 15 minutes the beads are washed over to a cultivating medium and the encapsulated cells are cultivated at 37° C.

EXAMPLE 8

Agarose is dissolved in PBS (5%, w/v) by heating. The polymer solution (5 ml) is brought to 37° C. and mixed with animal cells (5 ml), after which the mixture is dispersed in paraffin oil (40 ml). After cooling, the beads are washed over to a cultivating medium and the encapsulated cells cultivated at 37° C.

EXAMPLE 9

Collagen is dissolved in diluted hydrochloric acid. The polymer solution (cooled to 5° C., 2 ml) is mixed with 10 times concentrated medium and sodium hydroxide to obtain a neutral pH, and also with animal cells (2 ml). The mixture is dispersed in paraffin oil (40 ml). The mixture is gelled by heating to 37° C., the beads washed over to a medium and the encapsulated cells are cultivated at 37° C.

TABLE 1

The action of the hydrophobic phase on the respiration of plant cells encapsulated in agar

| Hydrophobic phase | Relative respiration (%) |
|---|---|
| Soybean oil | 100 |
| Tri-n-butyl phosphate | 100 |
| Paraffin oil | 91 |
| Liquid silicone | 100 |
| Phthalic acid dibutylester | 82 |
| Toluene: chloroform, (73:27 v/v), Arlacel 83 (2% w/v) | 0 |

TABLE 2

The action of the hydrophobic phase on polyacrylamide-encapsulated yeast cells.

| Hydrophobic phase | Relative respiration (%) |
|---|---|
| Soybean oil | 100 |
| Toluene: chloroform, (73:27 v/v) Arlacel 83 (2% w/v) | 7 |

We claim:

1. A method of immobilizing viable animal cells, plant cells, bacteria, algae or fungi with retained ability of growth by encapsulation in polymer beads, which comprises:
   (a) adding said viable animal cells, plant cells, bacteria, algae or fungi to an aqueous solution of agar, agarose or fibrinogen;
   (b) dispersing said aqueous solution in a non-toxic water-insoluble dispersion medium selected from the group consisting of soybean oil, tri-n-butylphosphate, liquid silicone, paraffin oil and phthalic acid dibutylester; and
   (c) allowing said agar, agarose or fibrinogen to gel to form polymer beads encapsulating said viable animal cells, plant cells, bacteria, algae or fungi either by cooling or by enzymatic action under conditions such that the growth ability of said cells is unaffected.

2. The method as claimed in claim 1, wherein said gelation is conducted so as to obtain beads having a granular size of 0.05–3 mm.

3. The method as claimed in claim 2, wherein said gelation is conducted so as to obtain beads having a granular size of 0.1–1.0 mm.

4. Immobilized viable animal cells, plant cells, bacteria, algae or fungi with a retained ability of growth, and being encapsulated in polymer beads of agar, agarose or fibrinogen, and being produced by:
   (a) adding said viable animal cells, plant cells, bacteria, algae or fungi to an aqueous solution of agar, agarose or fibrinogen;
   (b) dispersing said aqueous solution in a non-toxic water insoluble dispersion medium selected from the group consisting of soybean oil, tri-n-butylphosphate, liquid silicone, paraffin oil and phthalic acid dibutylester; and
   (c) allowing said agar, agarose or fibrinogen to gel to form the polymer beads encapsulating said viable animal cells, plant cells, bacteria, algae or fungi such that the growth ability of said cells is unaffected.

5. The method as claimed in claim 1, wherein said retained growth ability of said cells is such that after the encapsulation of said viable animal cells, plant cells, bacteria, algae or fungi, a relative respiration in the range of 82-100% is exhibited.

6. The immobilized cells as claimed in claim 5, wherein the retained growth ability of said cells is such that after the encapsulation of said viable animal cells, plant cells, bacteria, algae or fungi, a relative respiration in the range of 82-100% is exhibited.

* * * * *